US00PP09159P

United States Patent [19]

Laver

[11] Patent Number: Plant 9,159

[45] Date of Patent: Jun. 13, 1995

[54] MINIATURE ROSE PLANT NAMED 'LAVLING'

[75] Inventor: Keith G. Laver, Ontario, Canada

[73] Assignee: Bear Creek Gardens, Inc., Medford, Oreg.

[21] Appl. No.: 293,711

[22] Filed: Aug. 22, 1994

[51] Int. Cl.[6] ..... A01H 5/00

[52] U.S. Cl. ..... Plt./8.2

[58] Field of Search ..... Plt. 24, 8.2, 7.1

[56] References Cited

U.S. PATENT DOCUMENTS

P.P. 7,136 2/1990 Laver ..... Plt./8.2

P.P. 8,030 11/1992 Laver ..... Plt./8.2

*Primary Examiner*—Howard J. Locker

*Attorney, Agent, or Firm*—Klarquist Sparkman Campbell Leigh & Whinston

[57] ABSTRACT

A miniature rose plant having the unique combination of a bright-yellow flower color; easy production from softwood cuttings; healthy, mildew-resistant foliage; and a shelf life of 12 to 14 days.

1 Drawing Sheet

1

The present invention relates to a new and distinct variety of rose plant of the miniature class which was originated by me by crossing Loving Touch (as the seed parent) and an unnamed seedling (as the pollen parent) resulting from the cross of Dorola×Genevieve (U.S. Plant Pat. No. 5,145).

The primary objective of this breeding was to produce a new rose variety having a bright yellow, non-fading color; good growth habits for pot rose production and an acceptable shelf life (i.e. duration of bloom flush or period of maintenance of bloom). The objective was substantially achieved, along with other desirable improvements, as evidenced by the following unique combination of characteristics that are outstanding in the new variety and that distinguish it from its parents, as well as from all other varieties of which I am aware:

1. Bright-yellow flower color;
2. Easy to produce from softwood cuttings;
3. Healthy, mildew-resistant foliage; and
4. A shelf life of 12 to 14 days.

Asexual reproduction of this new variety by softwood cuttings, as performed at Wasco and Somis, Calif., shows that the foregoing characteristics and all other features come true to form and are established and transmitted through succeeding propagations.

The accompanying illustration shows typical specimens of the vegitative growth and flowers of this new variety in different stages of development, depicted in color as nearly true as it is reasonably possible to make the same in a color illustration of this character.

The following is a detailed description of my new rose cultivar with color descriptions using terminology in accordance with the Royal Horticultural Society (London) Colour Chart, except where ordinary dictionary significance of color is indicated.

Parentage:

*Seed parent.*—Loving Touch.

*Pollen parent.*—Unnamed seedling (Dorola×Genevieve).

Classfication:

*Botanical.*—*Rosa hybrida.*

*Commercial.*—Miniature.

2

FLOWER

Observations made from specimens grown in a greenhouse environment at Somis, Calif., from January to April 1994.

Blooming habit: Recurrent.

Bud:

*Size.*—½ inch long when the petals start to unfurl.

*Form.*—The bud form is pointed ovoid.

*Color.*—When sepals first divide, bud color is Yellow Group 13C. When half brown, the upper and lower sides of the petals are Yellow Group 13 C;

*Sepals.*—Color: Green Group 138C. Surface Texture: Covered in fine hairs. There are three lightly appendaged sepals. There are two appendaged sepals with hairy edges.

*Receptacle.*—Color: Yellow-Green Group 164B. Shape: Funnel. Size: Small (⅛ inch×⅛ inch). Surface: Smooth.

*Peduncle.*—Length: Short (1 to 1¼ inches). Surface: Smooth. Color: Light green. Strength: Stiff, erect, slender.

Bloom:

*Size.*—Small. Average open size is 1¼ to 1½ inches.

*Borne.*—Singly.

*Stems.*—Short, strong. Average length is about 4 to 6 inches.

*Form.*—When first open: Flat. Permanence: Flattens, outer petals curl back.

*Petalage.*—Number of petals under normal conditions: 25.

*Color.*—The upper sides of the patals are Yellow Group 13C. The reverse sides of the petals are Yellow Group 13C. The base of the petals is Yellow Group 13C. The major color on the upper sides is Yellow Group 13 C.

*Variations.*—None.

*Discoloration.*—The general tonality at the end of the first day: No change. At the end of the third day: No change.

*Fragrance.*—Slight.

Petals:

*Texture.*—Thin.

*Shape.*—Oval.

*Form.*—Tips slightly recurved, edges slightly quilled.

*Arrangement.*—Imbricated, with a few petaloids in the center.

*Persistance.*—Drop off cleanly.

*Lastingness.*—On the plant: Fair (7 to 9 days).

Reproductive parts:

*Anthers.*—Size: Small. Quantity: Many. Color: Yellow. Arrangement: Regular around styles.

*Filaments.*—Color: Yellow.

*Pollen.*—Color: Lemon yellow.

*Styles.*—Color: Reddish pink.

*Stigmas.*—Color: Greenish white.

Form: Bush.

Growth: Vigorous, dwarf, upright, branching, compact. Size at maturity is 10 to 12 inches in height.

Foliage: Number of leaflets on normal mid-stem leaves: 5 or 7.

*Size.*—Small (2 to 2½ inches × 1¼ inches).

*Quantity.*—Abundant.

*Color.*—New foliage: Yellow-Green Group 146A. Old foliage: Green Group 137B.

Leaflets:

*Shape.*—Pointed oval.

*Texture.*—Upper side: Smooth.

*Edge.*—Serrated.

*Serration.*—Single, small.

*Petiole rachis.*—Color: Green.

*Petiole underside.*—Smooth, with an occasional prickle.

*Stipules.*—Medium, serrated, bearded.

*Disease resistance.*—Resistant to mildew under normal greenhouse growing conditions at Somis, Calif.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—Medium, straight.

*Color when young.*—Green.

Small prickles:

*Quantity.*—On main stalks: None. On laterals: None.

I claim:

1. A new and distinct variety of rose plant of the miniature class, substantially as herein shown and described, characterized particularly as to novelty by the unique combination of its bright-yellow flower color; easy production from softwood cuttings; healthy, mildew-resistant foliage; and a shelf life of 12 to 14 days.

* * * * *

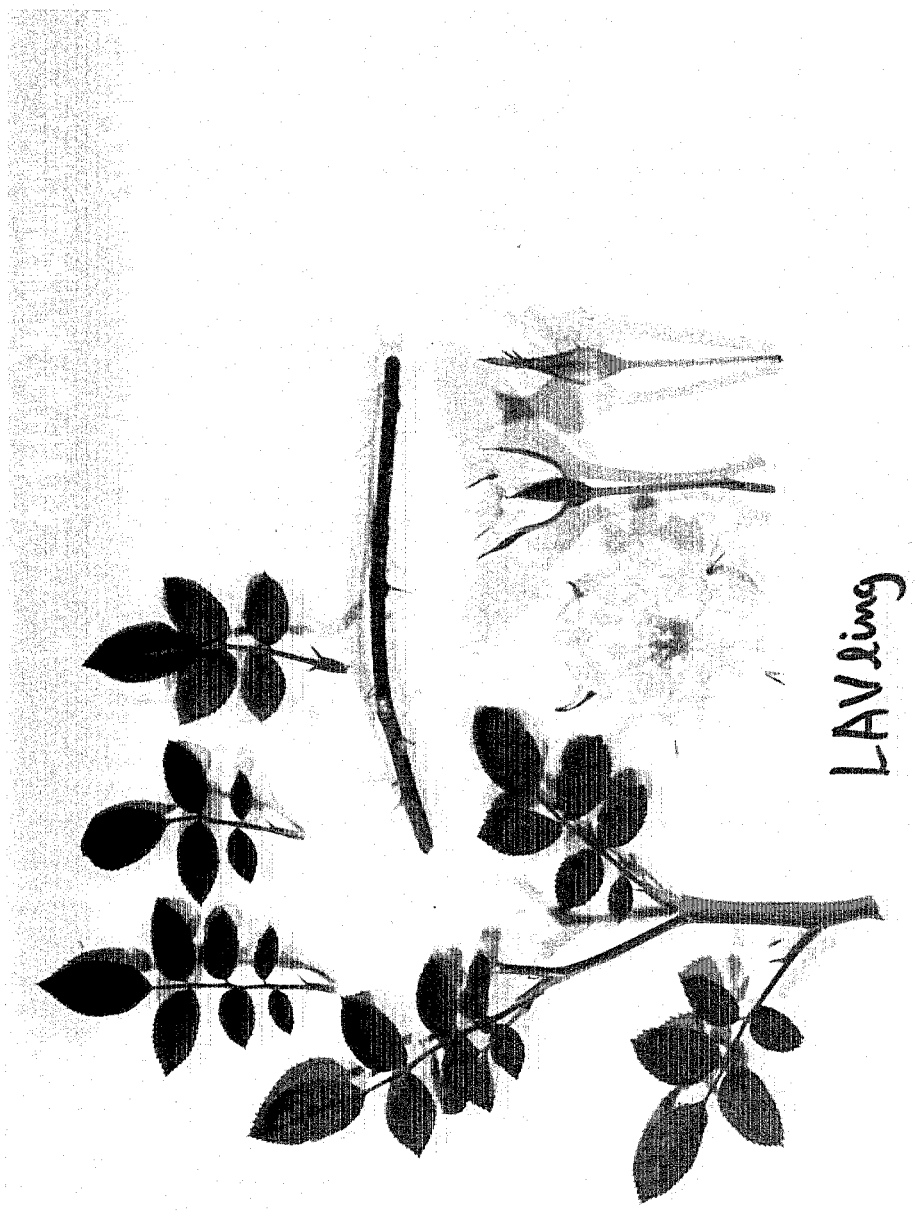
LAVling